United States Patent [19]
Mercereau

[11] Patent Number: 5,529,738
[45] Date of Patent: Jun. 25, 1996

[54] METHOD OF MAKING A PLUNGER CAP

[76] Inventor: Steven F. Mercereau, 4911 W. Lake Dr., Conyers, Ga. 30208

[21] Appl. No.: 367,452

[22] Filed: Dec. 30, 1994

Related U.S. Application Data

[62] Division of Ser. No. 172,736, Dec. 27, 1993, Pat. No. 5,377,689.

[51] Int. Cl.⁶ ..................................... B28B 5/00
[52] U.S. Cl. .................... 264/250; 264/266; 264/267; 264/274; 264/275; 264/279
[58] Field of Search ...................... 264/250, 266, 264/267, 275, 279, 274; 425/111, 129.1, 112

[56] References Cited

U.S. PATENT DOCUMENTS

| | | | |
|---|---|---|---|
| 3,608,049 | 9/1971 | Tavella | 264/229 |
| 4,041,934 | 8/1977 | Genese | 128/2 F |
| 4,299,238 | 11/1981 | Baidwan et al. | 128/763 |
| 4,361,155 | 11/1982 | Anastasio | 128/763 |
| 4,373,535 | 2/1983 | Martell | 128/765 |
| 4,448,206 | 5/1984 | Martell | 128/765 |
| 4,466,446 | 8/1984 | Baidwan et al. | 128/765 |
| 4,485,065 | 11/1984 | Hatakeyama et al. | 264/255 |
| 4,660,569 | 4/1987 | Etherington | 128/765 |
| 4,690,154 | 9/1987 | Woodford et al. | 128/765 |
| 4,703,763 | 11/1987 | McAlister et al. | 128/765 |
| 4,732,162 | 3/1988 | Martell | 128/765 |
| 4,766,908 | 8/1988 | Clement | 128/765 |
| 4,774,963 | 10/1988 | Ichikawa et al. | 128/763 |
| 4,821,738 | 4/1989 | Iwasaki et al. | 128/765 |
| 4,934,379 | 6/1990 | Marzolf et al. | 128/765 |
| 5,108,381 | 4/1992 | Kolozsi | 604/319 |
| 5,238,003 | 8/1993 | Baidwan et al. | 128/765 |
| 5,275,953 | 1/1994 | Bull | 436/69 |

*Primary Examiner*—Jan H. Silbaugh
*Assistant Examiner*—Robin S. Gray
*Attorney, Agent, or Firm*—Kennedy & Kennedy

[57] ABSTRACT

A method for making a plunger cap for use with a sampling syringe for collecting a blood sample, in which an elongated tube open at one end communicates with a sampling needle attached at the other end. A plunger rod with a plunger cap slidably inserts into the open end of the tube. The plunger cap comprises a body that encloses an air permeable filter. A front portion of the body slidably contacts the inner wall of the tube for forming a fluid-tight first seal. The plunger cap includes means for forming a fluid-tight second seal spaced from the first seal. The second seal is effected by elastically deforming the body from a first position to a second position. Blood, being communicated through the needle into the tube by moving the plunger rod axially away from the needle, displaces air rearwardly through the filter against the second seal. The air then escapes from the tube upon return of the second seal to its first position. The plunger cap is manufactured by injecting a resilient air impermeable plastic into a void around the filter in a mold, the plastic also communicating through an axial bore in the filter. The pressure of the injection in the bore is then redirected radially outward to flex the filter into the void being filled with the plastic.

3 Claims, 3 Drawing Sheets

METHOD OF MAKING A PLUNGER CAP

This is a division of application Ser. No. 08/172,736 filed Dec. 27, 1993, now U.S. Pat. No. 5,377,689.

TECHNICAL FIELD

This invention relates to sampling syringes. More particularly, the present invention relates to a seal for a sampling syringe and method of manufacture.

BACKGROUND OF THE INVENTION

One mechanism for monitoring the health of medical patients is blood gas analysis. This is a commonly performed procedure in the healthcare industry. A blood sample can be obtained from either a vein or an artery of a patient, depending on the information to be determined. The blood sample is then tested to determine information about the health of the patient. This information includes the content of the blood gas, for example, oxygen and carbon dioxide, and of ionized elements, for example, ionized calcium, sodium, and potassium. The status of the patient is determined by comparing the determined values from the sample to "normal" values.

A blood sample is obtained using a sampling syringe. The sampling syringe comprises an elongated tube open at one end with a hypodermic needed attached at the other end for communication with the tube. A plunger rod extends into the open end of the tube. A plunger cap attaches to the end of the plunger rod that inserts into the tube. The plunger cap facilitates drawing the sample of blood, as discussed below, and seals the sample from communication, for example, with the atmosphere, to prevent contamination and spilling of the sample from the syringe. Typically the plunger cap comprises an air impermeable body that encloses a self-sealing air permeable filter. The body forms a seal at a front end of the plunger. The front end includes an inlet into the filter which communicates with an exit port. A second seal closes the exit port for a purpose discussed below.

A syringe with venting capability is commonly used for drawing a blood sample from a patient. The venting syringe allows displaced air from the needle and the tube to vent to the atmosphere from the tube through the exit port. Closing the exit port with the second seal facilitates obtaining a fluid sample by aspiration, as discussed below. The sample is held in a sample chamber in the tube. The sample chamber is defined by the front face of the plunger cap and the end of the tube to which the needle is attached.

After a sample is drawn, the plunger cap then seals to prevent communication into and out of the tube. To do this, the filter includes a hydrophilic gelatin. When blood contacts the filter, the gelatin absorbs some of the blood fluids and solidifies to seal the plunger cap. This seal blocks fluid flow through the plunger cap. This protects the sample from contaminants in the atmosphere and reduces the transfusion of dissolved gases between the blood sample and atmosphere. The sealing action prevents blood from leaking out of the syringe through the vent. The seal also protects the sample from contamination by ambient air entering into the tube. Contamination of the sample or transfusion of the dissolved gases between the sample and the atmosphere results in incorrect analysis of the sample. This may lead to incorrect diagnosis and treatment.

The venting syringe is used to obtain fluid samples, such as blood, from a patient. In addition to venting and sealing, the sampling syringes have other needs that arise from how the syringe is used to obtain the sample. Particularly, sampling syringes are used to aspirate the patient for filling the sample chamber with blood, and the sampling syringes are used to pulsate self-fill with a sample. As discussed above, the sampling syringe must vent to allow displaced air to escape when the blood enters the sample chamber of the tube. The venting of displaced air occurs during or after collection of the blood sample. For example, during collection of an arterial blood sample, therapists typically preset the plunger rod in the tube for a desired sample size. The sample chamber in the tube is full of air. The needle is inserted into the target artery. Blood then begins to fill the sample chamber and displace the air. The air escapes from the tube through the exit port in the plunger cap.

Some fluid samples from patients are obtained by aspiration. This technique is particularly important for obtaining a blood sample from a patient with low blood pressure. During collection of a venous blood sample or an arterial blood sample from a patient with low blood pressure, the blood must be aspirated, or pulled, into the tube. The sampling syringe therefore must create a vacuum when the plunger assembly is pulled outwardly. For this to happen, the vent path in the plunger cap must close, or air will flow into the tube during withdrawal of the plunger rod. This would prevent the syringe from forming the vacuum. The vacuum is necessary to physically aspirate blood from the patient, through the needle, and into the collection chamber of the tube.

Aspiration to obtain a blood sample is performed by positioning the plunger cap fully within the tube against the tube wall where the hypodermic needle attaches. The needle is inserted into the patient and the plunger rod pulled outwardly. The second seal forms a fluid-tight seal that blocks communication through the plunger cap. The movement of the plunger rod creates a vacuum within the sample chamber. The vacuum aspirates, or pulls, the blood from the patient into the sample chamber.

Once the blood sample has been collected by aspiration, or by pre-set venting discussed above, a bubble of air typically lies between the blood sample and the port in the plunger cap. This bubble of air comes from the air in the needle and the syringe lower tip between the needle and the plunger cap. This bubble of air must be evacuated from the sample chamber with minimal contact to the blood sample. To leave or mix the air bubble with the blood would contaminate the sample.

The bubble of air is expelled in two ways. One way is to point the needle upwardly. This causes the air bubble to float through the blood sample up to the needle. The air can be expelled through the needle by advancing the plunger. This forces the air and some blood outwardly, preferably into an absorbent material for disposal. This method, however, has significant drawbacks. If an air bubble travels through the blood sample, the entire sample will be contaminated by diffusion of gases between the air bubble and the blood. Also, blood-borne pathogen presents a hazard from blood spray and from accidental needle sticks.

Venting syringes prevent these problems by expelling the air through the open end of the tube. The needle tip is first plugged with a standard needle stopper or cap. The plunger rod is then advanced inwardly against the air bubble and the collection chamber. The air bubble is thereby forced out through the exit port of the plunger cap without further contact with the blood. To do this, the second seal must open to allow the air to escape. The capability to vent through the plunger cap therefore must be reversible. First, the second seal must close to aspirate the blood sample from the patient. Second, the seal must open to discharge the air bubble which can contaminate the sample.

As the plunger rod moves inwardly into the sample chamber, the air escapes through the exit port. The plunger rod then contacts the meniscus of the blood sample. Upon contact with the blood fluids, the gelatin in the filter rapidly cures to seal the plunger cap.

For patients with sufficiently high blood pressure, therapists often allow the sampling syringe to self-fill under the pulsating pressure of the blood in the arteries. The plunger assembly accordingly must move outwardly in response to the blood filling the tube at normal blood pressure. In this practice, therapists use the syringe with the plunger assembly initially advanced completely inward. This positions the plunger cap against the inner end wall of the tube where the hypodermic needle attaches. The needle is then inserted into the target artery. Blood flows under arterial blood pressure into the syringe. This displaces the small amount of air trapped in the needle and the needle hub on the syringe. The air escapes through the exit port in the plunger cap and the blood contacts the plunger cap. The hydrophilic gelatin in the filter reacts with the blood, and seals the plunger cap from further communication. This accomplishes the purposes discussed above of the plunger cap and minimizes the time the blood is exposed to contaminating air. Accordingly, venting sample syringes must move the plunger assembly outwardly as the syringe self-fills, until the blood flow is stopped by removing the syringe or until the plunger rod stops moving. Typically sampling syringes that are capable of pulsating self-fill include a stop inside the syringe tube. The stop halts the movement of the plunger rod when the sample chamber is filled.

The prior art describes sampling syringes which have venting plunger caps. Typically, the plunger caps includes flexible frustoconical sealing elements at the longitudinal ends. The sealing elements project axially and outwardly into engagement with an inside surface of the syringe for forming a fluid-tight seal. One plunger cap has a longitudinal channel formed in the body which communicates with an air permeable filter held in a front portion of the cap. The channel includes a seat in an opening adjacent the filter. A ball is disposed in the channel. Upon holding the syringe at a predetermined angle, the ball falls against the seat to block air communication through the plunger cap.

Another plunger cap includes a rearwardly-facing annular surface that partially closes a cavity in the cap. The plunger rod connects to the plunger cap by inserting a tip into the cavity. The tip attaches to a neck that extends from an end of the plunger rod. The thickness of the annular surface is less than the length of the neck, thereby permitting axial movement of the plunger cap with respect to the tip. An air-tight seal is defined by bringing a forwardly-facing surface of the tip into contact with the rearwardly-facing annular surface.

Another plunger cap includes passageways that extend through the cap for communicating air from the sample chamber out of the syringe. The passageways each include a hydrophilic thread which swells in contact with blood fluids for blocking communication through the passageways. This plunger cap provides venting but is unable to aspirate a sample.

The plunger caps for the sampling syringes described above are manufactured by one of two methods. One method molds the body of the plunger cap the filter in place. The other method molds the body and the filter separately. The two components are then assembled by inserting the filter into the body. Each method has benefits and drawbacks. When molding in place, the high temperature and the high pressure of the injected material for the body compresses the filter together. The filter material softens and compresses. This reduces the size of the pores through which the air communicates through the filter. The effectiveness of the plunger cap for venting air and for aspirating samples is lessened. On the other hand, separate manufacture and assembly requires additional labor. The plunger cap using the ball valve is believed to be manufactured in place, with the ball being inserted. Further, defective assembly of the plunger cap may prevent the plunger cap from forming the seal sufficient to aspirate a sample. The defective syringe causes additional discomfort to a patient who must have a second needle insertion to obtain the one sample, after the defective syringe is disposed of.

It is thus seen that a need remains for a plunger cap that vents displaced air from a sample chamber, that seals the vent for aspiration of a sample, and that pulsate self-fills a sample from a patient, with a method of manufacture that offers the benefits of mold-in-place manufacturing without the drawbacks that limit the effectiveness of the venting through the plunger cap, in a more effective and efficient manner. It is to the provision of such that the present invention is primarily directed.

SUMMARY OF THE INVENTION

In a preferred form of the invention, a sampling syringe for collecting a blood sample comprises an elongated tube open at one end and in communication with a sampling needle attached at the other end. A plunger rod with a plunger cap attached at a first end slidably inserts into the open end of the tube. The plunger cap comprises an air impermeable body that encloses an air permeable filter. The filter includes an inlet and an exit port for communicating air through the plunger cap. A front portion of the body has slidable contact with the inner wall of the tube for forming a fluid-tight first seal. The plunger cap includes means for forming a fluid-tight second seal spaced from the first seal. The second seal is effected by deforming the body from a first position to a second position. The deformation is preferably elastic, thereby permitting reversal of the seal from the second position to the first position. In a preferred embodiment, the plunger rod is withdrawn axially away from the needle, thus deforming the plunger cap elastically to effect the second seal and to create a vacuum for aspirating the blood sample. After obtaining the sample, the second seal returns to its first position which releases the vacuum.

In another preferred form of the invention, a method is disclosed of making a plunger cap for a sampling syringe. The plunger cap comprises an air impermeable body that encloses an air permeable filter. The filter includes an inlet and an exit port for communicating air through the plunger cap. The method comprises positioning a molded filter having an axial bore from a first end to a second end on a portion of a bottom surface of a mold. The bottom surface tapers down and outwardly from the portion to the inner wall of the mold. This portion defines a first seal at a forward end of the plunger cap. The mold is then covered with a plate having a core pin projecting downwardly from the plate into the interior of the mold. The core pin defines a cavity in the body. Means is provided for covering a portion of the filter for an exit port. A sprue extends through the plate. A resilient air impermeable plastic is then injected through the sprue into the mold for filling a void around the filter while leaving uncovered the inlet and the exit port in the filter. The plastic communicates through the bore to the bottom surface. The flow of the plastic is then redirected radially outwardly along the length of the bore. This flexes the filter outwardly into the void that is being filled with the plastic for defining the body around the filter.

DETAILED DESCRIPTION

Figure 1:
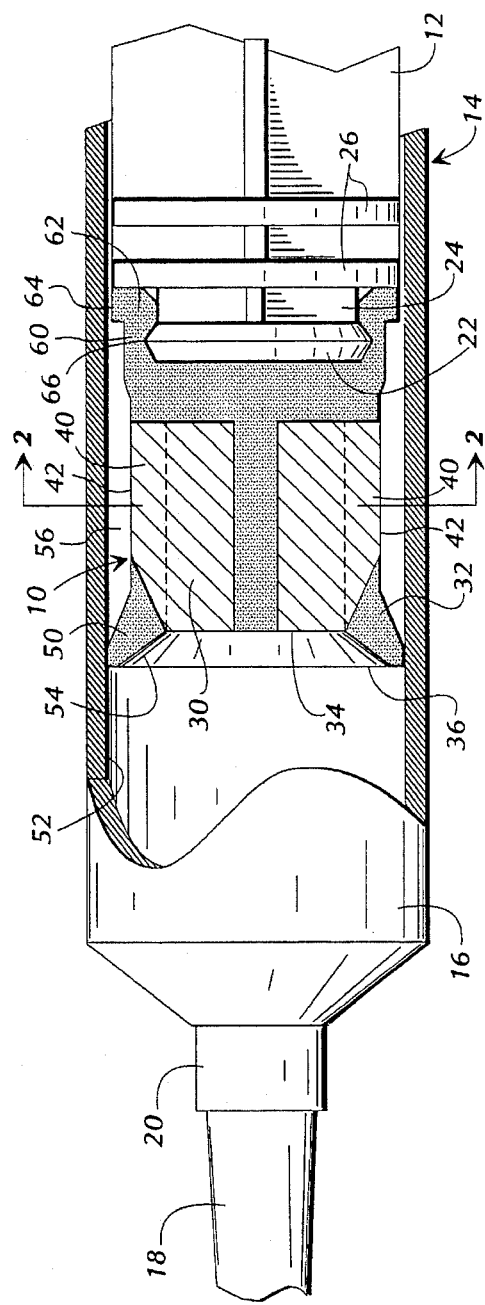
FIG. 1 is a side cut-away view of a plunger cap that embodies principles of the invention in a preferred form inserted into a sampling syringe.

Referring now in more detail to the drawings, in which like numerals indicate like parts throughout the several views, FIG. 1 shows a side cut-away view of a plunger cap 10 according to the present invention for attachment to a plunger rod 12 that inserts into a sampling syringe 14. The syringe 14 comprises an elongated tube 16 with a needle 18 connected to a needle hub 20 at one end of the syringe. The needle 18 is a conventional hypodermic needle for communication through the needle hub 20 to the tube 16. The plunger rod 12 has an elongated portion which is cross-shaped in cross-sectional view. A flat disc 22 attaches to a stem 24 at a first end of the plunger rod 12. For rigidity and support, a pair of spaced-apart plates 26 extend outwardly from the plunger rod 12 near the distal end of the plunger rod. The plunger cap 10 connects to the disc 22 of the plunger rod 12 to form a plunger assembly. The plunger assembly slidably inserts into the interior of the tube 16, as discussed below.

Figure 3:
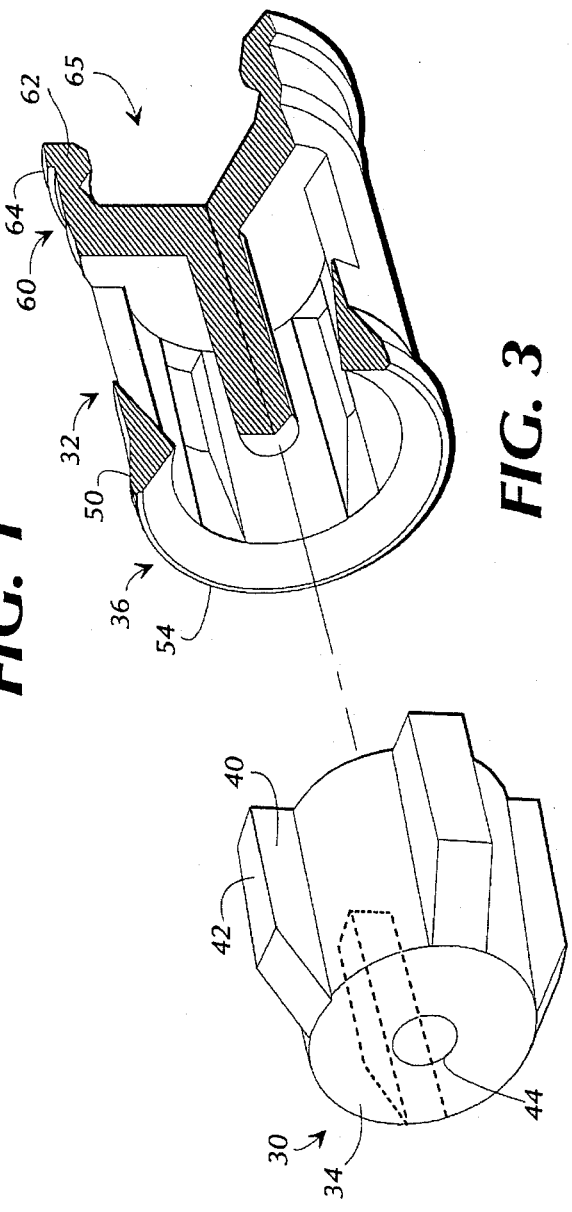
FIG. 3 is an exploded perspective view of the plunger cap of FIG. 1 cut-away to illustrate details.
Figure 2:
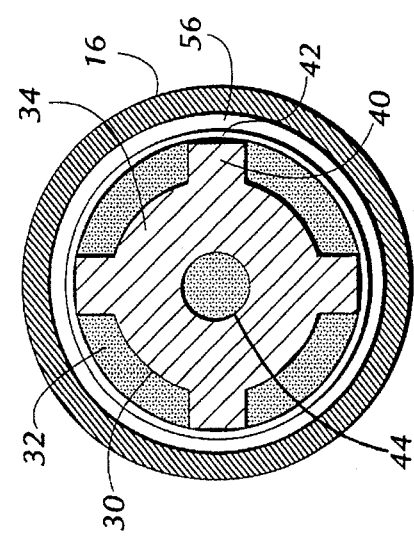
FIG. 2 is a cut-away end view of the plunger cap taken along line 2—2 of FIG. 1 for illustrating details thereof.

FIGS. 2 and 3 show the plunger cap 10 in end view and exploded perspective view, respectively. The plunger cap 10 comprises a filter vent 30 and a body 32. The filter vent 30 is made of an air permeable material. The body 32 is made of an air impermeable plastic. The filter vent 30 has a face 34 at a front portion 36 of the plunger cap 10. As illustrated in FIG. 2, the filter vent 30 is generally cross-shaped in cross-sectional view. The filter vent 30 has a cylindrical body 38 with four arms 40 extending radially to the surface of the body 32. The distal ends of the arms 40 define ports 42 in the wall of the body 32. A bore 44 extends coaxially through the filter vent 30. As illustrated in FIG. 1, the bore 44 is filled with the plastic material comprising the body 32, as discussed below. The front portion 36 of the body 32 includes an annular axially extending flange 50 that contacts the inner wall 52 of the tube 16. The front portion 36 of the body 32 thereby is in slidable contact with the inner wall 52 for forming a fluid-tight first seal 54. The diameter of the front portion 36 of the body 32 is greater than that of an intermediate portion 55 of the body. This defines a gap 56 between the surface of the body 32 and the inner wall 52, for a purpose discussed below.

The plunger cap 10 includes a fluid-tight second seal 60 spaced from the first seal 54. The second seal 60 is effected by deforming the body 32 elastically from a first position to a second position. In the illustrated embodiment, the fluid-tight second seal 60 comprises an axially extending annular flange 62 at a second end of the plunger cap 10. An outer surface 64 of the annular flange 62 is normally spaced apart from the inner wall 52 for defining an annular gap between the flange 62 and the wall 52 of the tube 16. The annular flange 62 further defines a cavity 65 in the plunger cap 10 for receiving the disc 22 on the plunger rod 12. The cavity 65 corresponds in shape and size to the disc 22. The cavity 65 defined by the annular flange 62 facilitates connecting the plunger cap 10 to the plunger rod 12.

The annular flange 62 elastically moves to a second position by bulging outwardly about an edge 66 of the disc 62. In the illustrated embodiment, the flange 62 bulges outwardly in response to a pulling pressure on the plunger rod 12 combined with a dragging force imposed by the first seal 54 of the plunger cap 10 against the wall 52 of the tube 16. The outward expansion of the flange 62 brings the surface 64 into contact with the inner wall 52 of the tube 16. The flange 62 balloons outwardly into sealing contact with the inner wall 52. This effects the second seal 60 of the plunger cap 10 and blocks communication through the gap 56, for a purpose discussed below.

Figure 4:
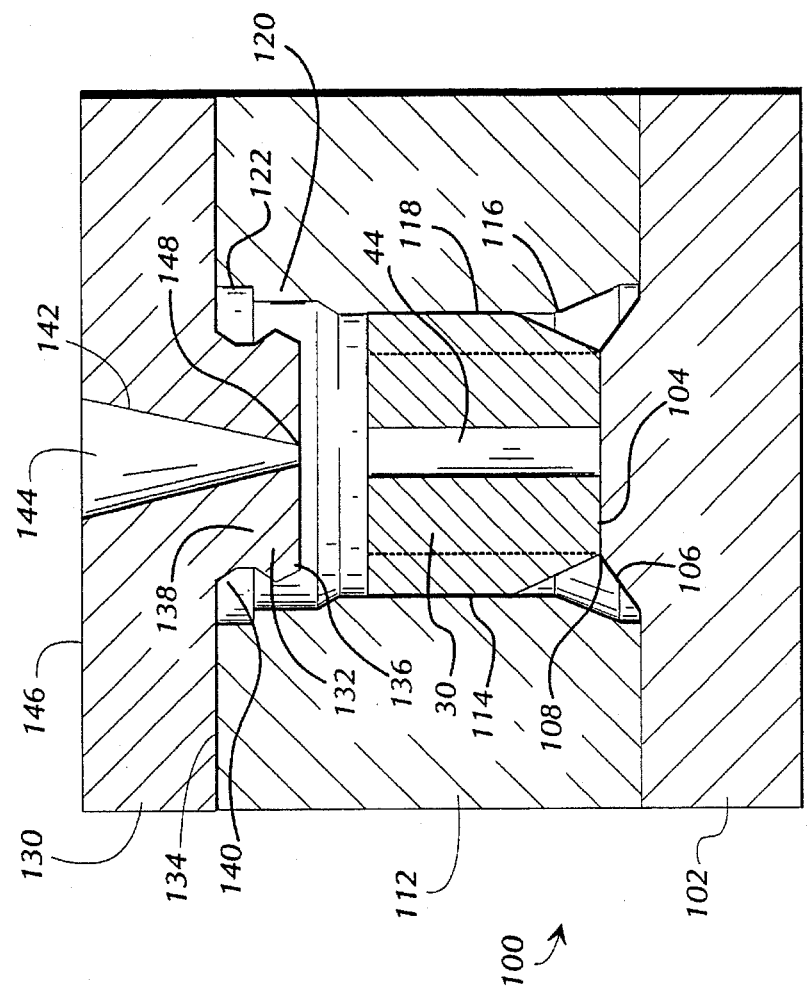
FIG. 4 is side view of a mold for manufacturing the plunger cap of FIG. 1.

FIG. 4 is a side view of a mold generally designated 100 for manufacturing the plunger cap 10 shown in FIG. 1. The mold 100 has a bottom plate 102 with a raised platform 104. The platform 104 is circular to correspond to the face 34 of the plunger cap 10. A surface 106 of the plate 102 tapers down and outwardly from an edge 108 of the annular platform 104. The annular platform 104 and the tapered surface 106 define a bottom surface in the mold 100. An alternate embodiment (not illustrated) of the mold is provided for the filter vent 30 that defines an exit port in a back face instead of including the radial arms 40 with the distal ends 42 as exit ports. A pin projects upwardly from the platform 104. The pin inserts into the bore 44 for positioning the filter vent 30 in the mold 100.

A second plate 112 having an annular cavity 114 is positioned on the plate 102. A lower portion 116 of the cavity 114 flares outwardly. The diameter of the portion 116 is greater than the diameter of a main portion 118. An upper portion 120 of the cavity 114 has a diameter intermediate the portion 118 in the lower portion 116. In the illustrated embodiment, the upper portion 120 includes a notch 122 having a slightly greater diameter than that of 120. The annular cavity 114 receives an air impermeable plastic, as discussed below, for forming the body 32 of the plunger cap 10.

A cover plate 130 is received on the plate 112 to close the annular cavity 114. The plate 130 includes a core pin 132 that projects downwardly from a bottom surface 134 of the plate 130. The core pin 132 in cross-section corresponds to the shape of the disc 22 and the stem 24 of the plunger rod 12 illustrated in FIG. 1. The core pin 132 accordingly comprises a disc 136 and a stem 138 connected to the plate 130. The stem 138 has a tapered shoulder 140 between the surface 134 and the stem 138. A sprue 142 extends through the plate 130 and the core pin 132. The sprue 142 tapers from an opening 144 in an upper surface 146 of the plate 132 to a narrow opening 148 in the core pin 132. The sprue 142 is coaxial with the annular cavity 114, for a purpose discussed below.

To manufacture the plunger cap 10 of the present invention, a filter vent 30 is molded of an air permeable material.

Molding the filter vent 30 is conventional in the art. The filter vent 30 further includes a conventional gelatin material for reacting with water to form a rigid seal in the filter vent 30 which then is impervious to fluid flow. In a preferred embodiment the filter vent 30 is made of a material having formula number FN 37-8-43 available from Interflow Technologies, Inc. of Brooklyn, N.Y.

The plate 112 with the cavity 114 is placed on the plate 102. Alignment pins and bores (not illustrated) align the plates 112 and 102 so that the cavity 114 is coaxial with the annular platform 104. The molded filter vent 30 is placed in the cavity 114. The front face 34 of the filter vent 30 makes intimate contact with the surface of the platform 104. The four arms 40 extend outwardly and the distal ends 42 contact the inner wall of the cavity 114.

The cover plate 130 is then positioned on the plate 112, with pins and bores (not illustrated) to align the respective plates. The core pin 132 thereby inserts into and occupies a portion of the void in the cavity 114 between the filter vent 30 and the walls of the annular cavity 114. The plates are clamped rigidly together.

An air impermeable plastic material is then injected through the sprue to fill the void in the cavity 114. In a preferred embodiment, silicon is injected under high pressure and high temperature into the cavity 114. The opening 148 of the sprue 142 aligns with the bore 44 of the filter vent 30. The plastic flows from the sprue 142 into the bore 44 on the longitudinal axis of the filter vent 30. The plastic also begins filling the void between the filter and the wall of the annular cavity 114.

The plastic flowing into the bore 44 bottoms against the annular platform 104. As the plastic continues to flow into the cavity 114, the flow of the injected plastic is redirected radially along the length of the bore 44 through the filter vent 30. The filter vent 30 flexes under the pressure of the injected plastic into the void of the cavity 114 being filled with the resilient plastic. The flexing of the filter vent 30 into the void prevents the filter from becoming compressed directly against a firm surface by the pressure of the injected heated plastic. The flexing also forces the distal ends 42 firmly against the wall of the cavity. This keeps the distal ends 42 from being covered by the plastic. The face 34 in contact with platform 104 also remains uncovered by the plastic. The resilient plastic completely fills the void, including the lower portion 116 and the upper portion 120 of the annular cavity. The lower portion 116 of the cavity 114 accordingly forms the annular flange 50 at the front portion 36 of the plunger cap 10. The upper portion 120 defines the axially extending annular flange 62 at the other end of the plunger cap 10. The core pin 132 defines the cavity 65 for receiving the disc 22 of the plunger rod 12.

After the plastic cures to define the body 32, the mold 100 is opened. The cover plate 130 is removed and the core pin 132 pops outwardly from the molded plunger cap 10. The second plate 112 is separated from the bottom plate 102. The molded plunger cap 10 then is pushed outwardly from the cavity 114.

With reference to FIG. 1, the molded plunger cap 10 attaches to the plunger rod 12 by pushing the disc 22 into the annular cavity 65. The plunger cap 10 is encased in the air impermeable jacket with the face 34 of the filter vent 30 uncovered. The distal ends 42 of the arms are open in the surface of the body 32. The distal ends 42 accordingly define ports in the side wall of the body 32. The face 34 and the ports 42 in the filter vent 30 provide a path for communicating air though the plunger cap 10. The plunger assembly including the plunger rod 12 and the plunger cap 10 slidably inserts into the open end of the tube 16 for use as a sampling syringe.

The sampling syringe 14 incorporating the plunger cap of the present invention can then be used to obtain blood samples from a patient. The syringe 14 is capable of venting displaced air from the tube 16 to the atmosphere, aspirating a blood sample from a patient, and pulsating self-fill. The plunger rod 12 is set at a selected position along the length of the tube 16 to define a collection chamber of a desired sample size. The body of the tube 16 typically is imprinted or embossed with graduations for determining the size of the sample chamber. The sample chamber in the syringe 14 is full of air. The needle 18 is inserted into the selected artery of the patient. Blood then begins to fill the sample chamber displacing the air. The air escapes by passing through the face 34 of the filter vent 30 and exits through the ports 42 and the gap 56 rearwardly past the annular flange 62 to the atmosphere. The portion of the blood adjacent the displaced air also enters the filter vent 30. The hydrophilic gelatin in the filter vent 30 absorbs the blood and solidifies. As the entire face 34 and the interior portions of the filter vent 30 solidify, the filter vent 30 becomes sealed against further flow of fluids or air. This sealing action prevents blood from leaking out of the tube 16. It also protects the sample from contamination by ambient air coming back into the tube 16.

The plunger cap 10 of the present invention further facilitates aspirating a blood sample from a patient. In particular, aspiration is typically necessary during collection of a venous blood sample or of an arterial blood sample from a patient with low blood pressure. The plunger rod 12 is pushed into the tube 16 until the face 34 is close to the needle hub 20 of the syringe 14. The needle 18 is inserted into the vein or artery of the patient. The plunger rod 12 is slowly retracted to withdraw the plunger cap towards the open end of the tube 16. The pulling motion by the disc 22 against the annular flange 62, combined with the drag of the first seal 54, causes the body 32 to deform elastically. The annular flange 62 bulges outwardly forcing the face 64 against the inner wall 52 of the tube. This effects the second seal 60. The second seal is fluid-tight and accordingly the syringe 14 forms a vacuum as the plunger rod 12 is withdrawn from the tube 16. The vacuum pulls the blood sample through the needle and into the sample chamber of the tube 16.

When a sufficient sample has been taken, the pulling pressure on the plunger rod 12 is released. The body 32 relaxes to its first unsealed position. The second seal 60 is released as the annular flange 62 returns to the first spaced-apart position. This opens the gap 56 between the surface of the body 32 and the inner wall 54. The needle 18 is then extracted from the patient and closed with a conventional cap (not illustrated).

The contaminated bubble of air between the blood sample and the second seal 60 then is then vented to the atmosphere. The plunger rod 12 is depressed slightly to expel the air from the filter vent 30 and the sample chamber. The meniscus of the blood sample further enters the filter vent 30 through the face 34. The hydrophilic gelatin in the filter vent 30 absorbs the meniscus fluids and seals the sample chamber from the atmosphere, as discussed above.

The plunger cap 10 of the present invention also facilitates pulsating self-fill. This method of collecting a blood sample from a patient is more comfortable for the patient, in that the blood flows to the syringe by the normal blood pressure of the patient. The plunger rod 12 is fully pushed inwardly into the tube 16 to position the plunger cap 10 next to the needle hub 20. The needle 18 is then inserted to the target artery. The plunger rod 12 is released and the syringe 14 is gripped around the tube 16. Blood then flows into the syringe 14 under the normal blood pressure of the patient. The blood displaces the small amount of air trapped in the needle tip and the lower portion of the tube 16. As the blood continues to fill the sample chamber, the displaced air is vented through the face 34 and the ports 42. The air passes through the gap 56 to the atmosphere. The plunger rod 12 with the cap 10 is pushed away from the hub 20 by the pressure exerted by the blood. As blood fills the filter vent 30, the gelatin reacts with the blood to form a meniscus seal between the sample and the atmosphere. After the sample is obtained, the needle 18 is then withdrawn from the patient and closed with a conventional needle cap.

Figure 5:
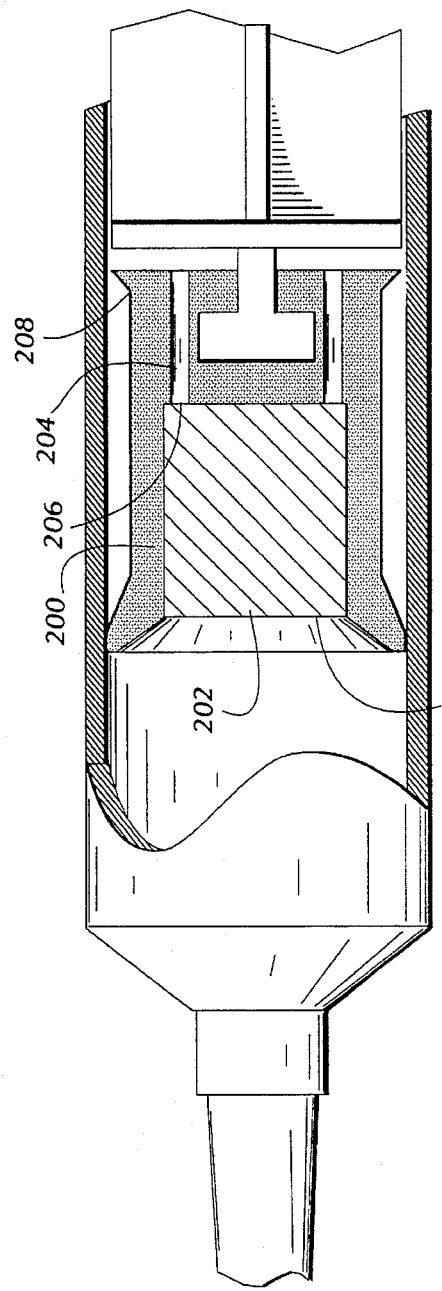
FIG. 5 is a side view of an alternate embodiment of the plunger cap of the present invention.
Figure 6:
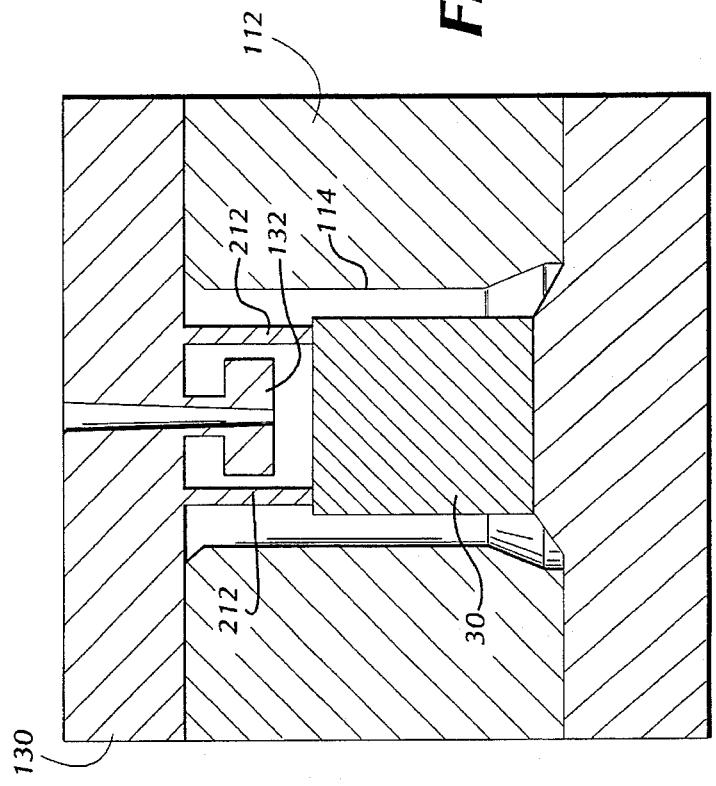
FIG. 6 is a side view of a mold for making the plunger cap of FIG. 5.

An alternate embodiment of the plunger cap 10 is shown in FIG. 5. The plunger cap 10 comprises a body 200 that encloses a porous self-sealing vent plug 202. The vent plug 202 has an open face 34 and communicates with at least one vent shaft 204. The vent shaft 204 extends from a back side 206 of the vent plug 202 to a back edge 208 of the body 200. Flexible frustoconical extensions 210 extend outwardly from the body 200 for contacting the inner wall 52 of the tube 16. The extensions 200 form seals between the plunger cap 10 and the tube 16. Air in the tube 16 accordingly communicates through the face 34 of the vent plug 202 and through the vent shafts 204. As illustrated in FIG. 6, the vent shafts 204 are defined in the body 200 by the projections 212 that extend downwardly from the plate 130 of the mold 100 for manufacturing the plunger cap 10.

When the plunger rod 12 is pulled outwardly from the tube 16, the body 200 of the plunger cap 10 deforms. The vent shafts 204 collapse and thereby prevent communication through the plunger cap 10. The plunger cap 10 thereby creates a vacuum when the syringe is used to aspirate a blood sample from a patient.

From the foregoing, it is seen that an improved plunger cap and method of manufacturing a plunger cap for a sampling syringe is disclosed. It should be understood that the above described embodiment merely illustrates principles of the invention in a preferred form. Many modifications, additions, and deletions may, of course, be made thereto without departure from the spirit and scope of the invention as set forth in the following claims.

What is claimed is:

1. A method of making a plunger cap having an air impermeable body that encloses an air permeable filter having an inlet port and an exit port for communicating air through the plunger cap, comprising:

positioning a face of said air permeable filter, having an axial bore from a first end therethrough to a second end, onto a portion of a bottom surface of a mold cavity in a mold, a lower portion of said mold cavity defining a first seal at a forward end of said plunger cap, said mold having means for covering a portion of said filter for defining an exit port on said plunger cap;

covering said mold cavity with a plate having a core pin projecting downwardly into said mold cavity for occupying a portion of a void in said mold cavity, with a sprue extending through said plate;

injecting a resilient air impermeable plastic through said sprue to flow into said mold cavity for filling said void around said filter while leaving uncovered said face of said filter positioned against said bottom surface of said mold cavity for providing an air permeable inlet port and while leaving uncovered a surface of said filter for providing an air permeable exit port in said filter for communicating air through said plunger cap, whereby said plastic communicates through said bore in said filter to said bottom surface of said mold cavity and said flow of said plastic being then redirected radially outwardly along said bore for flexing said filter outwardly into said void being filled with said plastic for defining said sealing body around said filter.

2. A method of manufacturing a plunger cap having a sealing body and an air permeable filter for attachment to an end of a plunger rod that slidably inserts into an open end of an elongated tube having a sampling needle attached at a different end for defining a sampling syringe, said plunger cap including a fluid-tight first seal and means for forming a fluid-tight second seal effected by deforming said sealing body of said plunger cap from a first position to a second position, comprising:

molding a filter having a cylindrical body, front face, and at least one arm having a distal end and extending radially from a side wall of said cylindrical body;

placing said front face of said filter on a raised annular platform defining a bottom surface in an annular mold cavity, the diameter of said platform being less than a diameter of said mold cavity, said bottom surface tapering down and outwardly from said raised annular platform to an inner wall of said mold cavity to define said first seal at a forward end of said plunger cap, said arms extending from said cylindrical body to said inner wall;

covering said mold cavity with a plate having a core pin projecting downwardly from said plate into said mold cavity for defining cavity in in said plunger cap for receiving a tip end of said plunger rod, with a sprue coaxial with said mold cavity extending through said plate and said core pin; and injecting a resilient plastic through said sprue and into said mold cavity for enclosing said filter in an air impermeable jacket leaving said distal ends of said arms and said front face of said filter on said annular plate uncovered by said jacket for communicating air into said sampling syringe and through said plunger cap.

3. A method of making a plunger cap with a fluid-permeable filter, comprising:

placing a first surface of said fluid-permeable filter on a lower surface in a cavity of a mold, said filter having a bore extending therethrough;

covering said mold with a plate from which a core pin depends for defining a flange in said plunger cap, said flange being for engaging said plunger cap to a plunger rod, said plate including at least one sprue therethrough for injecting a fluid-impermeable material into said mold cavity and around said filter, a portion of said mold being in intimate contact with a second surface of said filter;

injecting said resilient fluid-impermeable material through said sprue into said mold cavity for filling said bore and a void around said filter while leaving said first surface of said filter in intimate contact with said lower surface of said mold cavity for defining a fluid-permeable inlet to said filter and leaving said second surface of said filter in intimate contact with said mold for defining an exit from said filter, for communicating fluid through said plunger cap, whereby said fluid-impermeable material communicates through said bore in said filter to said lower surface in said cavity and said flow of said material being then redirected outwardly along said bore for flexing said filter outwardly into said void being filled with said plastic for defining said sealing body around said filter.

* * * * *